(12) United States Patent
Hasegawa (10) Patent No.: US 6,662,666 B2
(45) Date of Patent: Dec. 16, 2003

(54) INSTRUMENT AND METHOD FOR MEASURING PLUCK RESISTANCE OF FASTENER MEMBERS

(75) Inventor: Kenji Hasegawa, Tokyo (JP)

(73) Assignee: YKK Newmax Co., Ltd., Tokyo (JP)

( * ) Notice: Subject to any disclaimer, the term of this patent is extended or adjusted under 35 U.S.C. 154(b) by 0 days.

(21) Appl. No.: 10/102,217

(22) Filed: Mar. 20, 2002

(65) Prior Publication Data

US 2002/0144556 A1 Oct. 10, 2002

(30) Foreign Application Priority Data

Apr. 6, 2001 (JP) ........................................ 2001-108302
Dec. 26, 2001 (JP) ........................................ 2001-393794

(51) Int. Cl.⁷ ............................................... G01N 3/08
(52) U.S. Cl. ............................... 73/831; 73/830; 73/856
(58) Field of Search ..................... 73/831, 830, 862.01, 73/860, 856–859

(56) References Cited

U.S. PATENT DOCUMENTS 5,798,463 A * 8/1998 Doudican et al. ............. 73/789
5,798,467 A * 8/1998 Hasegawa et al. ......... 73/862.01

* cited by examiner

Primary Examiner—Edward Lefkowitz
Assistant Examiner—Jermaine Jenkins
(74) Attorney, Agent, or Firm—Wood, Phillips, Katz, Clark & Mortimer (57) ABSTRACT

This invention provides a pluck-resistance measuring instrument for fastener members comprises a holder for pressing the fabric of a garment to which a fastener member is attached, securely around the member, a plurality of clamp members capable of clamping the fastener member and moving at right angles to the place where the fastener member is affixed to the fabric, and a tension detector for measuring the tensile force that is applied to the clamp members, wherein the holder is supported by a lift, the tension detector comprises a member providing a fulcrum, a mass lever pivotally supported at the fulcrum and a tension detector, the lever being coupled at one end to the clamp members and acts on the tensile detector at the other end as a tensile detector and a method for measuring the pluck resistance using the above instrument comprises the steps of (1) starting the lift to lower the holder.

11 Claims, 5 Drawing Sheets

INSTRUMENT AND METHOD FOR MEASURING PLUCK RESISTANCE OF FASTENER MEMBERS

BACKGROUND OF THE INVENTION

This invention relates to an instrument and a method for measuring the resistance of the fastener members such as snap fasteners to plucking from the fabric of garments and the like to which they are attached.

Fastener members, such as snap fasteners each consisting of a female fastener member known as a socket and a male fastener member known as a stud (the two members for use as a combination being hereinafter called "fastener members") and fancy buttons, are in abundant use on garments and the like. Garment manufacturers today are required to assure certain pluck resistance of those fastener members as the Product Liability (PL) Act and regulations on small-size articles have come in force in the U.S. Of those fasteners, snap fasteners have a structure in which the male and female fastener members are resiliently engaged or disengaged, the members being attached opposite to each other to mate on overlapping edges of a garment fabric. Each fastener member is secured in place with a backing member known as a prong which consists of a flanged or annular base formed with several slender protrusions or prongs extending upright from the base. If a fastener member thus secured to the fabric comes off easily, an infant can swallow it or its backing member. To avoid this danger, each snap member or other similar fastener member must be guaranteed to resist plucking with forces at or beyond a predetermined level. For example, an official standard in Europe demands that a fastener pulled with a force of 90 N (newton) for 10 seconds should not come off the cloth to which it is secured. This standard has come to be accepted in this country too.

Inspection for pluck resistance, therefore, has become necessary at sewing factories. Now that the PL Act has been enforced in Japan too, testing of this character is imperative. Actually, however, the manufacturers are determining the pluck resistance by their own testing procedures, because the enforcement regulations do not stipulate the measuring method. Thus, much variation of the measured values presents a problem of the impossibility of proper evaluation.

We have already provided an instrument for measuring the pluck resistance of fasteners by Patent Application Kokai No. 9-37811. The instrument permits proper inspection with less variation than heretofore. The instrument (1) presses the fabric of a garment to which a fastener member (e.g., a socket or stud member of a snap fastener) has been attached with a prong or other backing member, securely around the fastener member; (2) while about the same time constrains the fastener member with forces exerted in the directions at right angles to the sides of the member; and (3) pulls the fastener member away in the direction at right angles to the surface of the fabric to which it is attached. To realize this sequence of steps, the instrument comprises means for pressing the fabric of a garment to which a fastener member is attached, securely around the member, means for constraining the sides of the socket member, tensile means for pulling the stud member away in the directions at right angles to the fabric surface to which the member is attached, and means for measuring the tensile force exercised by the tensile means.

For the measurement of pluck resistance there are two testing methods, destructive and non-destructive. Neither directly indicates the pluck resistance with individual garments to which test fastener members are attached. However, the measurement guarantees the pluck resistance of the fastener members made of the same material and by the same manufacturing steps. In the form of a nondestructive test, a fastener member may be pulled with a given (reference) tensile force, and if the member does not come off, then it is a concrete guarantee for the pluck resistance to plucking forces up to that limit. Conversely if the fastener is plucked off with forces below the limit, the test is destructive. The invention is thus applicable to the both tests, destructive and nondestructive. Moreover, the invention provides an instrument capable of testing, when desired, with tensile forces greater than the reference level.

The afore-described instrument has a disadvantage, however. Because its measuring means is designed to continuously indicate the numerical value of force, it is necessary to monitor constantly and determine pluck resistance and decide whether it is passable or not case by case. This presents little problem in sampling inspection but gives much inconvenience in total inspection where a large number of articles must at a time be inspected and judged whether they pass or not given tests.

The present invention is aimed at providing an instrument and a method for measuring snap resistance values of fastener members such as fastener members precisely, rapidly, and in a simple manner.

The aim of the invention is achieved by partial improvements in a measuring instrument as described in Japanese Patent Application Kokai No. 9-37811 (U.S. Pat. No. 5,798, 767). Parts like those described in the above literature will be briefly outlined here and reference should be had to the literature for details.

SUMMARY OF THE INVENTION

The present invention provides a pluck-resistance measuring instrument for fastener members which comprises holder means for holding a fabric of a garment to which a fastener member is attached, securely around the fastener member, a plurality of clamp members capable of clamping the fastener member and moving in the direction normal to the surface of the fabric where the fastener member is attached to the fabric, and tension detector means for measuring the tensile force that is applied to the clamp members, wherein said holder means is supported by lift means, said tension detector means comprises a member providing a fulcrum, a mass lever pivotally supported at the fulcrum and a tension detector, said mass lever being coupled at one end to said clamp members and adapted to act on the tension detector at the other end.

In a preferred embodiment of the invention, the tension detector is set so that it can detect a reference value of predetermined tension.

While the reference value may be detected using an electric switch as the tension detector that supports the other end of the lever, the tension detector in a preferred embodiment of the invention is a load cell and the other end of the lever rests on the load cell, the fulcrum and the mass distribution of the lever being set so that when the reference value has been attained the other end of the lever comes away from the load cell to no load.

In this aspect the load cell may be designed to determine tensile force up to the reference value.

Another embodiment of the invention uses a second load cell, and the other end of the lever is located beneath, and away from, the second load cell to determine any force above the reference value.

The invention also provides a method for measuring the pluck resistance of fasteners using the above instrument, which method comprises the steps of (1) starting the lift means to lower the holder means, (2) judging whether the force on the tension detector is at or above the reference value or not, (3) judging, if the force is below the reference value, whether the holder means has reached the lower limit position or not and, if it has not yet reached the lower limit position, repeating the above step (2), (4) reporting that the test piece has passed the inspection if the reference value is reached or exceeded in the step (2), and reporting that the test piece has failed if the lower limit position is reached in the step (3).

The invention further provides a measuring method comprising the above steps which further comprises the step of moving the lift means backward after the step (4) or (5) and, when the holder means has been reset to the upper limit position, stopping the lift means.

Moreover, the invention provides a measuring method which comprises the steps of (1) starting the lift means to lower the holder means, (2) judging whether the force on the tension detector is at or above the reference value or not, (3) judging, if the force is below the reference value, whether the holder means has reached the lower limit position or not and, if it has not yet reached the lower limit position, repeating the above step (2), (4) starting timing if the reference value is reached or exceeded in the step (2), judging again whether the force on the tension detector is at or above the reference value or not, and, if the force is at or above the reference value, reporting that the test piece has passed the inspection when the timing has reached a reference time, and (5) reporting that the test piece has failed if the lower limit position is reached in the step (3).

The method further comprises the step of moving the lift means backward after the step (4), (5) or (6) and, when the holder means has been reset to the upper limit position, stopping the lift means.

Further, the invention may further comprise the step of stopping the lift in the step (4) and, if the force is below the reference value, starting again the lift in the step (1).

DETAILED DESCRIPTION OF THE INVENTION

Figure 4:
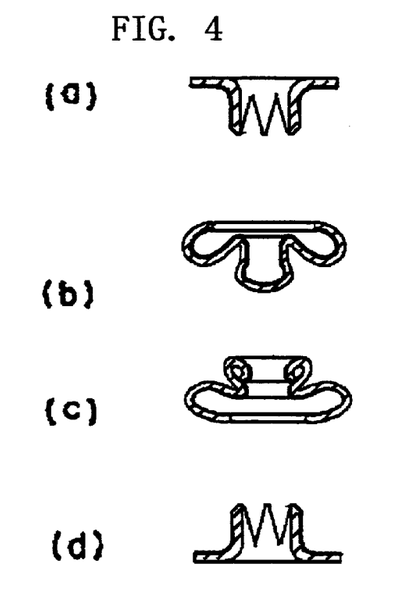
FIG. 4 is a diagrammatic view of different fastener members and backing members.

An embodiment of the present invention will be described in detail below with reference to the accompanying drawings. The embodiment is intended to illustrate the invention and is not to be construed to limit the scope of the invention. Although a snap fastener is shown in FIG. 4 as an example of fastener members, it should be obvious to those skilled in the art that the instrument of the invention can be used with other similar fastener members as well.

Embodiment 1

Figure 1:
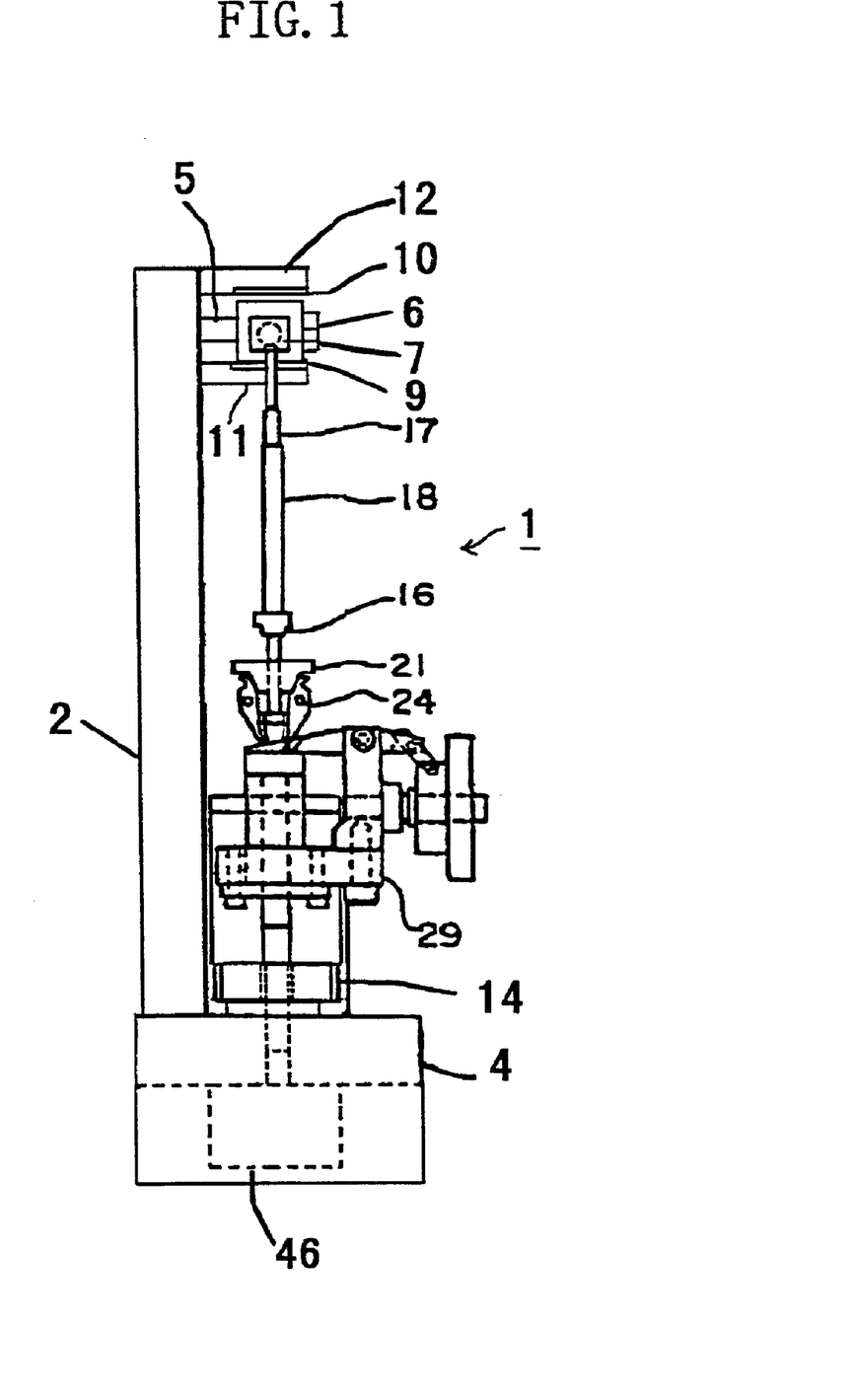
FIG. 1 is a front elevational view of a pluck-resistance measuring instrument embodying the present invention.
Figure 2:
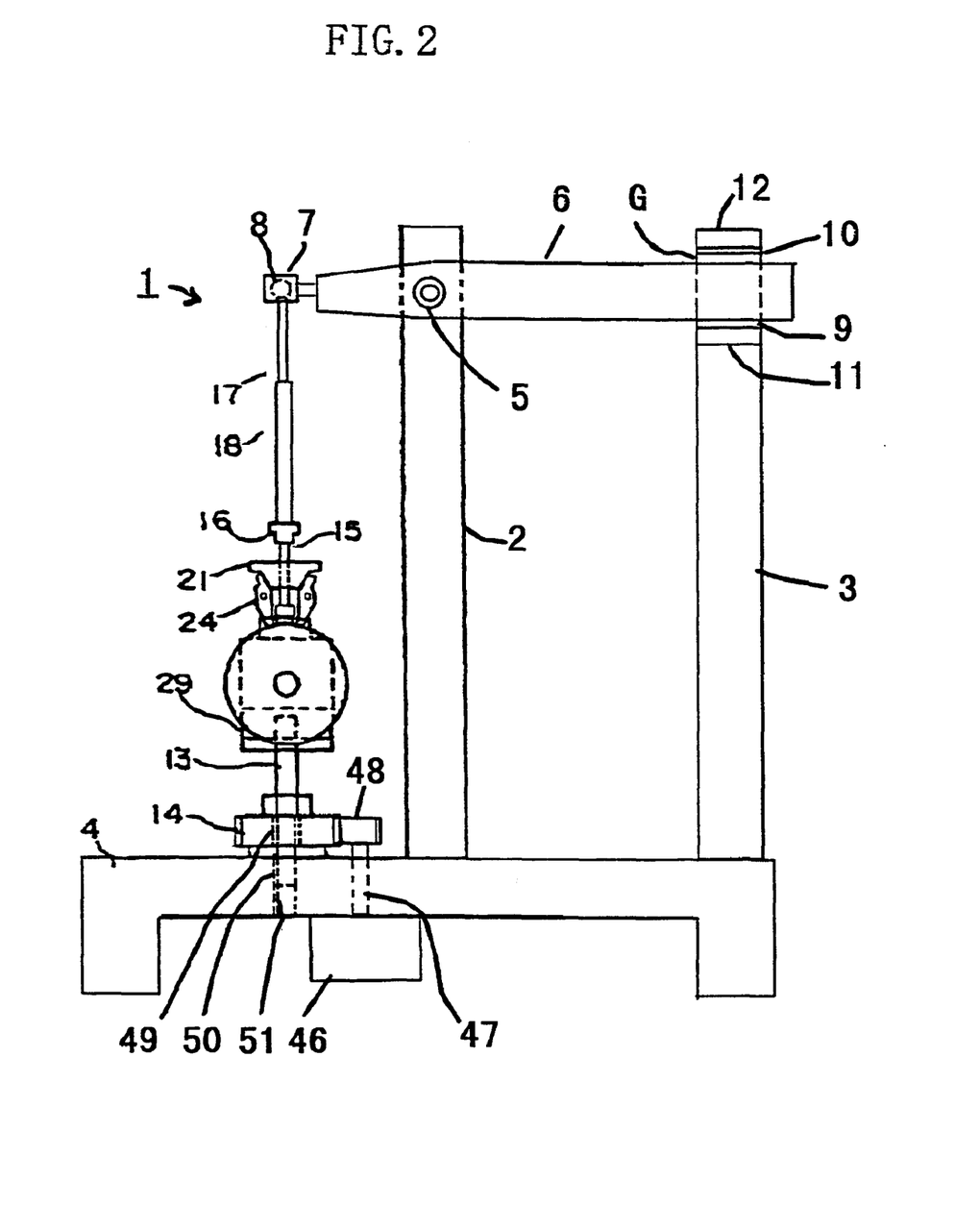
FIG. 2 is a right side elevational view of the instrument of the invention.
Figure 3:
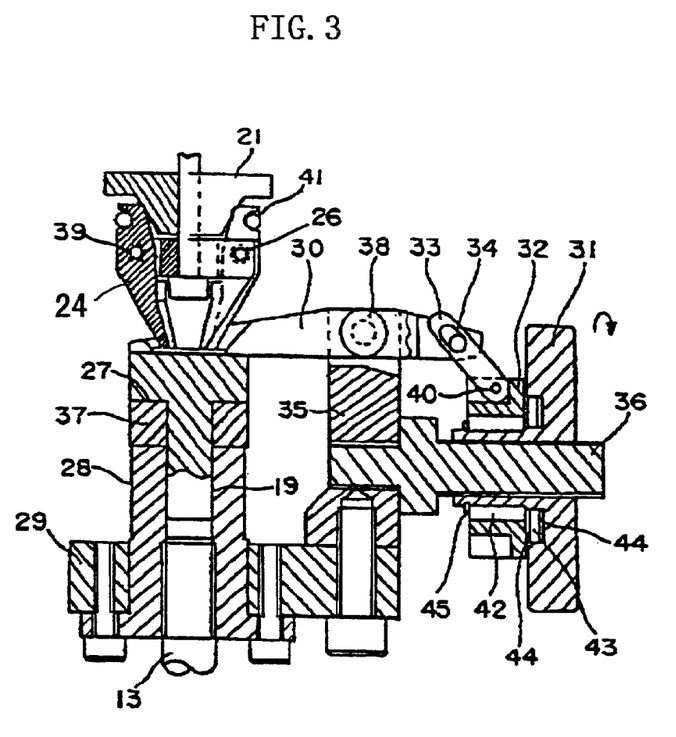
FIG. 3 is an enlarged front view, partly in section, of a part of the instrument of the invention.

FIGS. 1 and 2 generally illustrate a preferred embodiment of the pluck-resistance measuring instrument of the invention, FIG. 1 being a side view and FIG. 2 being a front view. FIG. 3 shows fastener clamp members, fabric-constraining or holder member, and a mechanism for operating those members. These are already known to the art and reference may be had to the afore-mentioned literature for particulars. They are explained here only where necessary. FIG. 4 shows a complete set of snap fastener components as an example of fastener that can be handled by the measuring instrument of the invention.

Referring to FIGS. 1 and 2, a fulcrum post 2 and a load cell post 3 both held upright on a base frame 4 are fixed in place with mounting means such as brackets (not shown). These members are made of a metal, e.g., aluminum. A pivot 5 is horizontally secured to a portion near the top of the post 2, and the pivot turnably supports a part near the left end of a weight lever 6, via bearing means such as ball bearings. Near the top end of the post 3, there are a lower support bracket 11 and an upper support bracket 12 extended frontward (as viewed in FIG. 2), carrying a lower load cell 9 and an upper load cell 10 secured to their opposing sides. A right end part of the weight lever 6 is received between the load cells 9 and 10 and is supported by the lower load cell 9. A slight gap G is provided between the upper surface of the lever 6 and the upper load cell 10. To the left end of the lever 6 is fixed a universal joint 7, which consists, e.g., of a hollow part having a spherical space and a ball 8 fitted in the space and is integrally connected to a rod or chain 17 suspended downwardly.

The position of the pivot 5 on, and the mass distribution of, the weight lever 6 are chosen so that at the equilibrium position of the lever 6, the force applicable to a clamp mechanism having clamp members to be described later is equivalent to the minimum guaranteed tensile force (e.g., the afore-mentioned 90-newton reference value) required of fasteners of this character. Where the gravity of the clamp mechanism is no small matter, appropriate compensation should be made for the gravity.

The chain 17 is sheathed in a resin tube 18 and is terminated at the lower end with a joint 16. The underside of the joint 16 has a vertical blind hole threaded internally, into which the upper end portion of an externally threaded vertical bolt 15 is screwed. The threaded bolt 15 carries at its lower end a set of jaws 24 and a jaw-adjusting dial 21 which altogether constitute tensile means to be detailed later.

A spur gear 14 is rotatably mounted on the upper surface of the base frame 4, and a support bolt 13 stands upright from the spur gear 14. The upper end of the support bolt 13 is in thread engagement with an internally threaded hole of a support block 29. The support block 29 supports a fabric-supporting stage of a testing table and means for pressing a fabric in position, both of which are to be described in detail below.

The details of the testing table and tensile means will now be described in conjunction with FIG. 3. FIG. 3 is an enlarged view, partly in section, of a frontal part of FIG. 1. A vertical cylindrical member 28 is fixedly mounted on the support block 29 with setscrews. A columnar leg 19 of a die 27 having a flat top surface to support a fabric and fastener members is inserted into the vertical bore of the vertical cylindrical member 28 through a flexible ring, e.g., of polyurethane rubber. This arrangement prevents the fabric presser means from exerting excessive pressure.

A presser arm 30 having an annular front end to press the fabric portion around a fastener member extends over the top surface of the die 27. The arm 30 is supported by a horizontal shaft 38, which in turn rests on an arm-supporting block 35 fixed integrally to the support block 29 with bolts. To the rear end of the presser arm 30 is connected the front end of a link 33 with a pin 34. The rear end of the link 33 is connected to a generally disk-shaped link holder 32. The link holder 32 has a groove to engage with the rear end of the link 33 and is constrained from turning, but it is movable along its central axis. The link holder 32 is supported, through a bearing 42, on a sleeve of an arm-adjusting dial 31 that is internally threaded and meshed with the external thread of a threaded horizontal shaft 36 fixed to the arm-supporting block 35. In FIG. 3, the numeral 45 designates a retaining washer for the link holder 32, 43 designates a thrust bearing for the dial 31, and 44, 44 are retaining washers.

Turning the dial 31 clockwise moves it leftward as viewed in FIG. 3, forcing the link holder 32 in the same direction, thereby urging the link 33 leftward. Thus the fabric presser arm 30 can turn counterclockwise pivotally around the horizontal shaft 38 to press the fabric with a fastener member located in the space of its annular front end. This dial may be designed to turn manually or automatically.

Next, the means for retaining the side faces of a fastener member will be explained. Referring to FIG. 2, the threaded bolt 15 is in thread engagement with the joint 16 connected to the lower end of the chain extending downward from the universal joint, as already described. The threaded bolt 15 has a large-diameter head formed at the lower end, which supports a horizontal jaw-supporting plate 26. Three jaws 24 are attached to the jaw-supporting plate 26 with horizontal pivot pins 39. As shown in FIG. 3, the jaws 24 are tapered at the lower end, with the inner side being nearly vertical. The jaws 24 have a circumferential groove each formed along the outer periphery, and a ring of coiled spring 41 is fitted in those grooves of the jaws 24 to bias the lower ends of the jaws normally in the open position. Above the jaws 24, the threaded bolt 15 extends through, in thread engagement with, an internally threaded hole of the jaw-adjusting dial 21, so that a truncated conical lower part of the bolt projecting downward can push apart the upper inner side portions of the jaws 24. Here again the jaw-adjusting dial 21 may be designed to turn manually or automatically.

With the construction described, turning the jaw-adjusting dial 21 clockwise round its vertical axis drives the jaws 24 pivotally on the horizontal pivot pins 39, whereby a fastener member is clamped in place.

Referring to FIG. 2, the support bolt 13 is made vertically movable by lift means now to be described. An electric motor 46 is mounted to the underside of the base frame 4 so as to turn a toothed wheel 48 fixed to the upper end of an output shaft 47 of the motor. Power is transmitted from the toothed wheel 48 to a spur gear 14 of a larger diameter in mesh with the wheel. The spur gear 14 is internally threaded along its center hole, in engagement with a male thread formed in the lower part of the support bolt 13. The lower end of the support bolt is a shaft portion not threaded but is formed with vertical splines 50. The splines are meshed with vertical grooves 51 in a hole of the base frame to constrain the support bolt so that the bolt can move up and down but not turn round.

Embodiment 2

Figure 6:
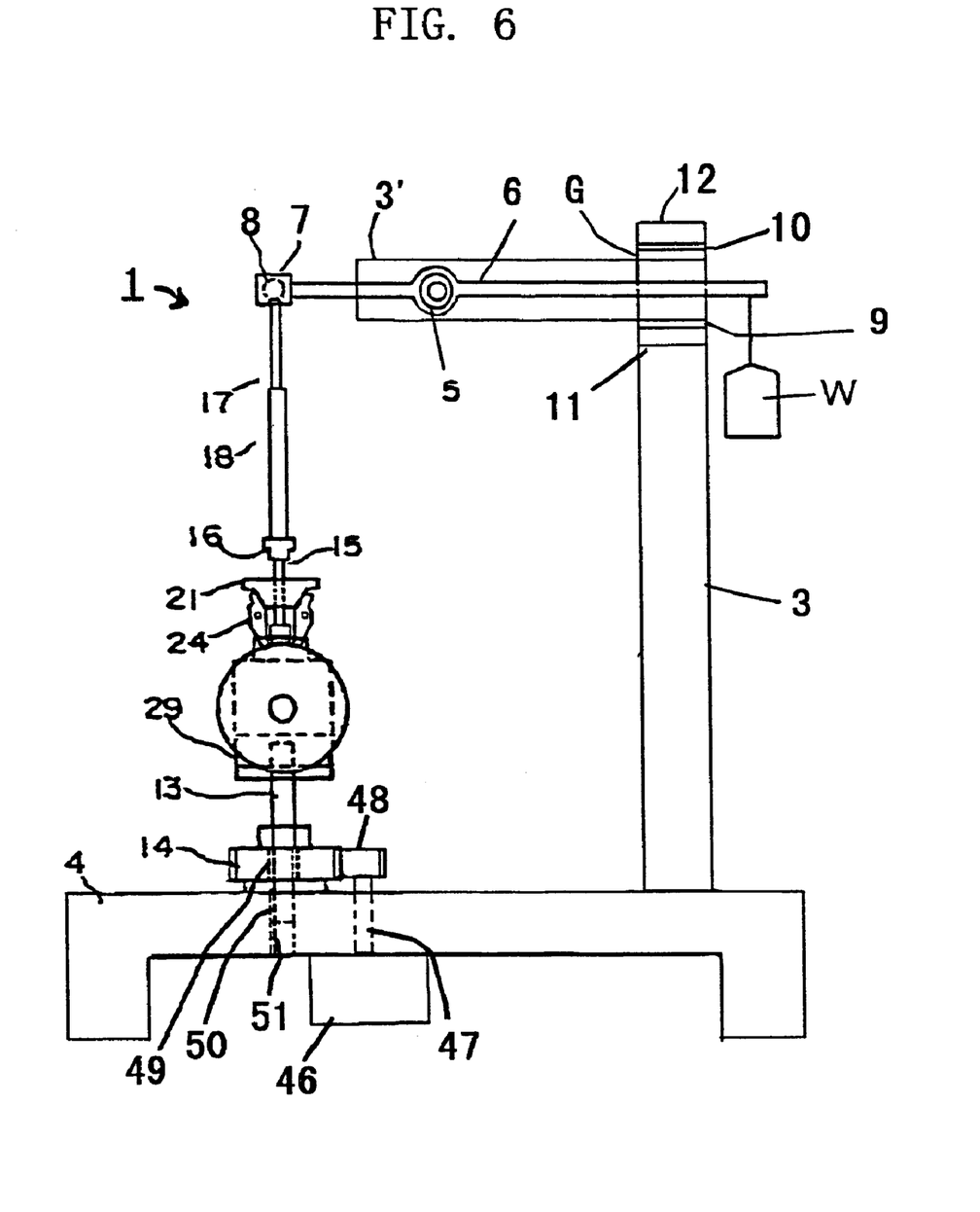
FIG. 6 is a view similar to FIG. 2 but showing a modified form of the invention.

FIG. 6 shows a modification of the embodiment of the invention. In place of the two posts 2, 3 in the first embodiment, a single post 3 is used in an inverted L-shape with a cantilever arm 3'. Near the free end of the arm 3' is provided a fulcrum pivot 5, which in turn supports a lever 6 of a limited mass. The front end of the lever is provided with a universal joint 7, and the rear end carries a weight W. The weight is suitably changeable with other weight, or an additional weight may be used. A plurality of weights may be exchangeably suspended from plural positions along the lever 6.

The upper end of the post 3 is provided with a pair of brackets 11, 12, and a load cell 9 is affixed to the lower bracket 11. An additional load cell 10 may be attached to the upper bracket 12 as well. The rest of the construction is the same as that of the embodiment described above.

This modified form requires a single post instead of two, and the arm 3' allows the fulcrum pivot 5 to be located closer to a fastener pulling mechanism. With a lower lever ratio, a smaller weight W can produce a greater moment of lever force, thus rendering it possible to reduce the size of the instrument.

Operational Example 1

As will be appreciated on the whole from the above explanation, the operation of the pluck-resistance measuring instrument for fastener members will be described in detail below. FIG. 4 illustrates various examples of snap fastener members to be tested. In the drawing, (a) and (d) are backing members of the same structure, each having prongs for securing a fastener member in place. (b) is a male snap member having an enlarged flange. (c) is a female fastener member likewise having an enlarged flange. For testing, a fastener member affixed to a fabric is placed on the surface of the die 27, in alignment with the axis of the threaded bolt 15, and the jaw-adjusting dial 21 is turned to clamp the sides of the fastener member in place with the jaws 24. Meanwhile the presser arm-adjusting dial 31 is turned until its annular end presses the fabric securely so as to hold the fastener attaching member beneath the fabric in position together with the fabric. Next, the motor 46 is switched on to turn the toothed wheel 14 and pull both the support bolt and the fabric holder mechanism supported by the bolt slowly downward.

It is now presumed that the fulcrum point and the mass distribution of the lever 6 are adjusted beforehand so that a tensile force of 90 N is applied to a test fastener member while the lever is in its equilibrium state. Then, when this reference value is exceeded, the load on the lower load cell 9 is naught and, at this point, the given pluck resistance is assured if the fastener remains unremoved from the fabric. If the fastener is plucked off before the above point is reached, it is off the standard or has failed to meet the requirement. The above requirement may be combined with a time factor; stopping the motor at the stage when the tensile force 90 N has been reached or exceeded, holding the state for 10 seconds, and seeing if the tensile force at or above 90 N is maintained. It is further possible either to indicate the value measured by the lower load cell by suitable display means or to report the zero load (indicating that the reference value has been attained) by some appropriate means, such as sound or visible display means. The latter, which tells each article that has passed the inspection, greatly facilitates the operation. Where the pluck resistance above the standard is to be measured, the upper load cell 10 is used and the measured value is suitably indicated by some display means.

Figure 5:
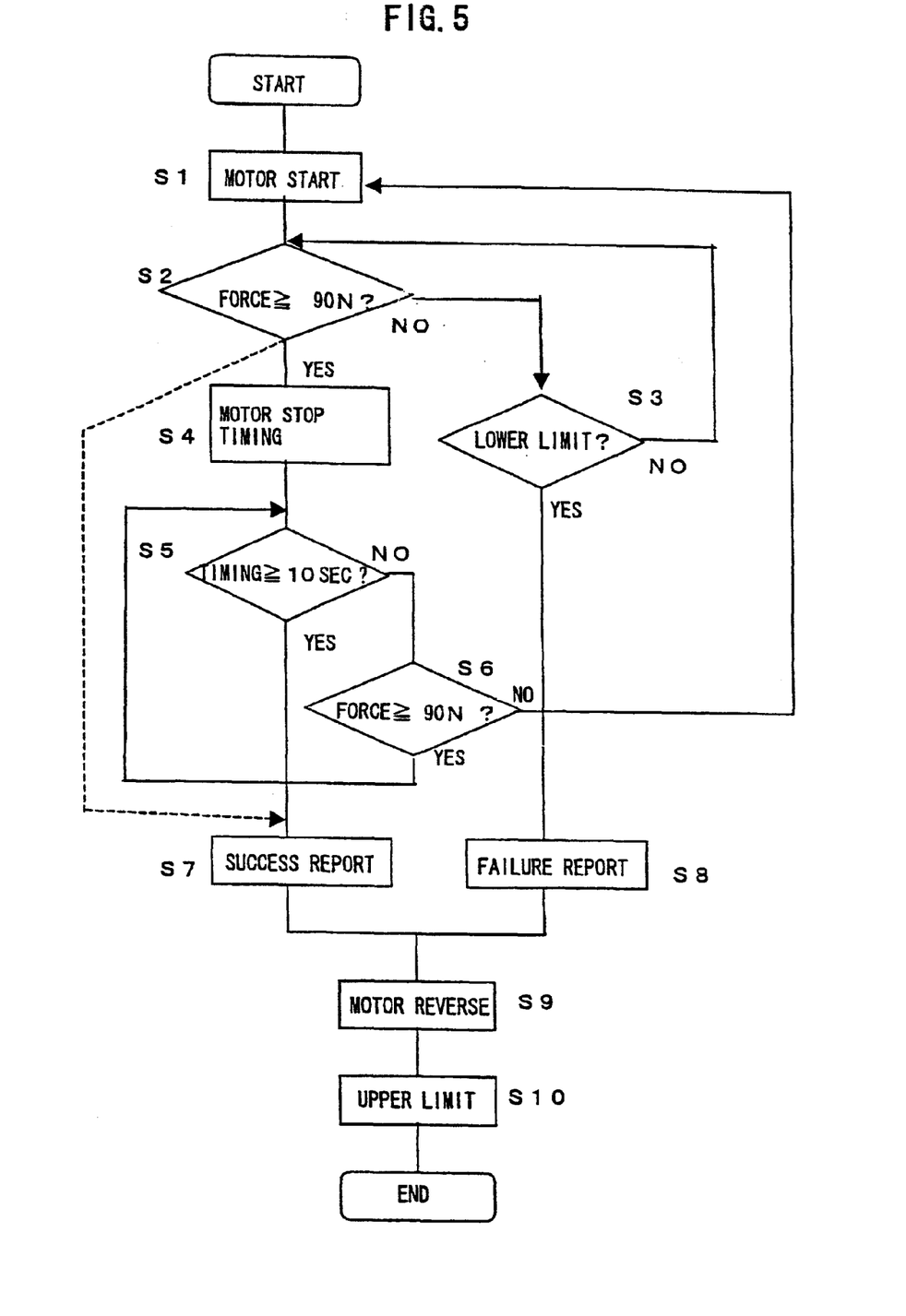
FIG. 5 is a flow chart of an example of the measuring method according to the present invention.

The above operation can be controlled in conformity with a computerized program. FIG. 5 illustrates a typical example. At the starting point where the fabric holder means is in its raised position, a test fastener member is set on the fabric holder, and the periphery of the member is held in place by the clamp means. First, a starting switch is turned on.

At the stage S1, the lift means to lower the holder means is started for a slow descent at a constant speed. The force the weight lever 6 applies to the lower load cell 9 is constantly monitored, and the value may be displayed by a gage or display unit via control means including an amplifier not shown. The lower load cell is initially subjected to the entire force at the end of the weight lever, and the load comes to naught at the point the reference value is attained. Hence the difference between the reference value and the measured value is a value corresponding to the tensile force that is applied to the test fastener member. At the stage S2, whether the tensile force is at or above the reference value (hereinafter referred to as 90 N) or not is determined, and if it is below 90 N, the operator makes it sure that the holder means is at its lower limit position, and if not the above stage S2 is repeated. On the other hand, if at the stage S2 the value is the same as or greater than 90 N, it is indicated via the broken line to the stage S7 where the passage of the inspection is reported by a speaker or colored lamp. If the lower limit position is reached at the stage S3, it means that the fastener has been plucked off the fabric before arrival at 90 N, and then the failure is reported at the stage S8.

Following the stage S7 or S8, the motor is reversed to raise the holder means at the stage S9. At the stage S10, a sensor or switch (not shown) that has returned to the upper limit position detects the reset position and stops the motor.

Operational Example 2

In the afore-described procedure, the flow represented by the broken-line route in FIG. 5 is replaced with one indicated by a solid line, and the tensile force during the reference holding time (hereinafter referred to as 10 seconds) with the reference load (hereinafter referred to as 90 N) is added for the measurement purpose. This stage may be performed, for example, with the servo control of the motor in the following way. If the stage S2 is YES or ≧90 N, the motor is stopped at the stage S4 and time counting is started. At the stage S5 cumulative counting is done for a unit time period (e.g., one second). When the cumulative count is less than 10 seconds, whether the force of the load cell at the stage S6 is at or above the reference value or not is determined. If it is below the reference value the cycle returns to the stage S1, where the motor is started again. If it is at or above the reference value the next unit time counting is done back at the stage S5. If the counting at the stage S5 is at least 10 seconds, the passage is reported at the stage S7. The procedure is repeated until at the stage S9 the lift means (motor) is reversed and, when the holder means is reset to the upper limit position at the stage S10, the lift means is stopped and the cumulative counter is cleared to conclude the whole cycle of operation. It is to be noted here that, once counting is started at the stage S4, the cumulative counter at the stage S5 should not be cleared until one complete cycle of inspection is concluded. This is because the test fastener has only to withstand the force of 90 N for a cumulative period of at least 10 seconds. Where necessary, however, the cumulative counter may be cleared upon each return to the loop of S4, for individual time counting. This is applicable where the test specimen is required to withstand a force at or above 90 N for an uninterrupted period of 10 seconds.

The afore-mentioned operational examples were directed to detection as to whether the fasteners to be checked satisfy the reference value of 90 N which is required for clearing the PL (product liability) regulations. However, the reference value may be very different from the exemplified snap fasteners depending on the types of the fasteners to be tested. For example, metal buttons or rivet/bars require a pulling force of 250 N or more to remove them from fabrics to which they have been attached. Such a change of the reference force can be easily done in the example illustrated in FIG. 6 by (1) replacing the weight with a different weight or (2) shifting the position the the same weight along the lever. If such a change is performed the control flow and the indicator setting has to be modified by, for example, switching between those for the reference value 90 N and that for 250 N.

This may be done in two ways. One method is done by modifying the instrument shown in FIG. 6 into that having an additional switch for switching between 90 N and 250 N and adding an additional weight or shifting the position of the same weight along the lever, while the flow diagram shown in FIG. 5 is modified in such manner that the S2 and S6 of FIG. 5 are used as they are for the reference value of 90 N while the reference value in the S2 and S6 is replaced by 250 N for the reference value of 250 N and the setting of the indicator is switched correspondingly.

Second method is done by changing the weight to that for 250 N in a condition that no pulling force is applied to the fastener member in position and full weight is applied on the lower load cell which senses the weight and automatically modify the sensitivity of the indicator correspondingly. Thus, in this example, there is no need of modifying the flow diagram of FIG. 5 and the reference value in the S2 and S6 is used as if the value was changed to 250 N.

While a preferred embodiment of the invention has so far been described, it should be obvious to those skilled in the art that various other modifications are possible without departing from the spirit of the invention.

Although the operational examples 1 and 2 used a computer for performing judgement or judgement and motor control, but basically load cells may be dispensed with if it is only necessary to tell whether a test piece has passed the inspection or not. Instead, simple on-off sensor switches may be provided at the points where the upper and lower load cells are otherwise located, in such a way that when the right end of the lever has moved out of contact with the lower switch or has come into contact with the upper switch, a voice signal is given.

It is also possible to provide means whereby an additional weight to adjust the balance of the lever is attached to the right end of the lever.

As will be clear from the foregoing description, the present invention uses a weight lever set to a predetermined tension and judges from the equilibrium position of the lever that the tension for pulling fastener clamp means and fabric holder means away from each other has reached a reference value. There is no need of meticulously watching the measuring means, and accordingly the efficiency of inspection is enhanced.

In the present invention, the load cells are not used in any portion through which the snap faster is pulled and thus the pulling force is not directly exerted on the load cells and when the reference force is exerted on the snap fastener the load on the load cells becomes zero and slight gaps is formed between the load cell and the load cells. The test piece may elongate during the holding period (the attached fastener can be loosened under the applied force). If such a phenomenon occurred and if the pulling force was directly applied to the load cells, a servo system would have to follow the change to compensate for this change. In the present invention, thanks to the gaps between the load cells and the end of the lever, a small elongation can be permissible within the gaps, and the operational example 1 (the flow diagram indicated by the dotted line of FIG. 5) and thus the more costly servo mechanism shown in the operational example 2 may be dispensed with. Also, if the elongation exceeds a predetermined value (the lever contacts the load cell) the motor may further continue to rotate in an extra amount without any servo mechanism.

The operational example 2 contains servo mechanism for such a case that the fastener requires a large stroke before the fastener is pulled off. Normally, the designing of the detection circuit according to the operational example 1 is sufficient.

What is claimed is:

1. A pluck-resistance measuring instrument for fastener members which comprises holder means for holding a fabric of a garment to which a fastener member is attached, securely around the fastener member, a plurality of clamp members capable of claiming the fastener member and moving in the direction normal to the surface of the fabric where the fastener member is attached to the fabric, and tension detecting means for measuring the tensile force that is applied to the clamp members, wherein said holder means is supported by lift means, said tension detecting means comprises a member providing a fulcrum, a mass lever pivotally supported at the fulcrum and a tension detector, said mass lever being coupled at one end to said clamp members and adapted to act on the tension detector at the other end, wherein the tension detector is a load cell and the other end of the lever rests on the load cell, the fulcrum and the mass distribution of the mass lever being set so that when the reference value has been attained the other end of the lever comes away from the load cell to no load.

2. The instrument of claim 1, wherein the tension detector is set so that it detects a reference value of predetermined tension.

3. The instrument of claim 2, wherein the load cell determines tensile force up to the reference value.

4. The instrument of claim 2, which further comprises means which, when the tension detector has detected any force above the reference value, maintains the force for a predetermined reference period of time.

5. The instrument of claim 1, which further comprises a second load cell and the other end of the lever is located beneath, and away from, the second load cell to determine any force about the reference value.

6. The instrument of claim 1, wherein the mass lever has a distributed mass.

7. A method for measuring the pluck resistance of fastener members using a measuring instrument which comprises holder means for holding a fabric of a garment to which a fastener member is attached, securely around the fastener member, a plurality of clamp members capable of clamping the fastener member and moving in the direction normal to the surface of the fabric where the fastener member is attached to the fabric, and tension detecting means for measuring the tensile force that is applied to the clamp members, wherein said holder means is supported by lift means, said tension detecting means comprises a member providing a fulcrum, a mass lever pivotally supported at the fulcrum and a tension detector, said mass lever being coupled at one end to said clamp members and adapted to act on the tension detector at the other end, said method comprising the steps of (1) starting the lift means to lower the holder means, (2) judging whether the force on the load cell is below the reference value or not, (3) judging, if the force is below the reference value, whether the holder means has reached the lower limit position or not and, if it has not yet reached the lower limit position, repeating the above step (2), (4) reporting that the test piece has passed the inspection if the reference value is exceeded in the step (2), and reporting that the test piece has failed if the lower limit position is reached in the step (3).

8. The method of claim 7, which further comprises the step of moving the lift means backward after the step (4) or (5) and, when the holder means has been reset to the upper limit position, stopping the lift means.

9. A method for measuring the pluck resistance of fastener members using a measuring instrument which includes holder means for holding a fabric of a garment to which a fastener member is attached, securely around the fastener member, a plurality of clamp members capable of clamping the fastener member and moving in the direction normal to the surface of the fabric where the fastener member is attached to the fabric, and tension detecting means for measuring the tensile force that is applied to the clamp members, wherein said holder means is supported by lift means, said tension detecting means comprises a member providing a fulcrum, a mass lever pivotally supported at the fulcrum and a tension detector, said mass lever being coupled at one end to said clamp members and adapted to act on the tension detector at the other end, said method comprising the steps of (1) starting the lift means to lower the holder means, (2) judging whether the force on the tension detector is at or above the reference value or not, (3) judging, if the force is below the reference value, whether the holder means has reached the lower limit position or not and, if it has not yet reached the lower limit position, repeating the above step (2), (4) starting timing if the reference value is reached or exceeded in the step (2), judging again whether the force on the tension detector is at or above the reference value or not, and, if the force is at or above the reference value, reporting that the test piece has passed the inspection when the timing has reached a reference time, and (5) reporting that the test piece has failed if the lower limit position is reached in the step (3).

10. The method of claim 9, which further comprises the step of stopping the lift in the step (4) and, if the force on the tension detector is below the reference value, starting again the lift in the step (1).

11. A pluck-resistance measuring instrument for fastener members which comprises holder means for holding a fabric of a garment to which a fastener member is attached, securely around the fastener member, a plurality of clamp members capable of clamping the fastener member and moving in the direction normal to the surface of the fabric where the fastener member is attached to the fabric, and tension detecting means for measuring the tensile force that is applied to the clamp members, wherein said holder means is supported by lift means, said tension detecting means comprises a member providing a fulcrum, a mass lever pivotally supported at the fulcrum and a tension detector, said mass lever being coupled at one end to said clamp members and adapted to act on the tension detector at the other end, wherein the mass lever comprises a bar and a weight mounted on the other end portion of the lever.

* * * * *